(12) United States Patent
Florent et al.

(10) Patent No.: US 12,694,528 B2
(45) Date of Patent: Jul. 28, 2026

(54) STENOSIS LOCALIZATION

(71) Applicant: KONINKLIJKE PHILIPS N.V., Eindhoven (NL)

(72) Inventors: Raoul Florent, Ville d'Avray (FR); Caroline Denise Francoise Raynaud, Suresnes (FR); Vincent Maurice André Auvray, Meudon (FR)

(73) Assignee: Koninklijke Philips N.V., Eindhoven (NL)

( * ) Notice: Subject to any disclaimer, the term of this patent is extended or adjusted under 35 U.S.C. 154(b) by 468 days.

(21) Appl. No.: 18/013,297

(22) PCT Filed: Jun. 24, 2021

(86) PCT No.: PCT/EP2021/067426
§ 371 (c)(1),
(2) Date: Dec. 28, 2022

(87) PCT Pub. No.: WO2022/002765
PCT Pub. Date: Jan. 6, 2022

(65) Prior Publication Data

US 2023/0274437 A1 Aug. 31, 2023

(30) Foreign Application Priority Data

Jul. 2, 2020 (EP) .................................... 20290053

(51) Int. Cl.
*G06T 7/00* (2017.01)
*A61B 6/12* (2006.01)
(Continued)

(52) U.S. Cl.
CPC .............. *G06T 7/0016* (2013.01); *A61B 6/12* (2013.01); *A61B 6/504* (2013.01); *G06T 7/174* (2017.01);
(Continued)

(58) Field of Classification Search
CPC ......... G06T 7/0016; G06T 7/174; G06T 7/38; G06T 7/70; G06T 2207/10121;
(Continued)

(56) References Cited

U.S. PATENT DOCUMENTS 10,664,970 B2 5/2020 Auvray et al.
2011/0216092 A1* 9/2011 Florent .................... G06T 5/50 345/634

(Continued)

FOREIGN PATENT DOCUMENTS

CN 110998744 A 4/2020
WO 2017016885 A1 2/2017

OTHER PUBLICATIONS

Brendo et al., "Algorithmic Solutions for Live Device-to-Vessel Match", In Proceedings of SPIE—vol. 5370—Medical Imaging 2004: Image Processing, J. Michael Fitzpatrick, Milan Sonka, Editors, May 2004, pp. 1486-1497.

(Continued)

*Primary Examiner* — Jennifer Mehmood
*Assistant Examiner* — Dustin Bilodeau

(57) ABSTRACT

The present invention relates to localizing stenoses. In order to provide improved and facilitated stenosis localization, a device (10) for localizing a stenosis in an angiogram is provided. The device comprises an image supply (12), a data processor (14) and an output (16). The image supply is configured to provide a first image (18) and a second image (20). The first image is an angiographic image that comprises image data representative of a region of interest of a vascular structure in a visible and distinct manner, wherein the vascular structure comprises at least one vessel with at least a part of a stenosis. The second image is a treatment X-ray image that comprises image data representative of at least a part of an interventional device arranged within the vascular structure in a state when the stenosis of the vascular
(Continued)

structure is treated. The data processor is configured to identify and delineate the stenosis in the first image based on the first image and at least based on device-related content present in the second image. The data processor is also configured to detect the interventional device in the second image, and to provide a direct identification of structures in the first image that are most similar to the device as detected in the second image. The output is configured to provide an indication of the stenosis.

15 Claims, 3 Drawing Sheets

(51) Int. Cl.

| | |
|---|---|
| ***A61B 6/50*** | (2024.01) |
| ***G06T 7/174*** | (2017.01) |
| ***G06T 7/38*** | (2017.01) |
| ***G06T 7/70*** | (2017.01) |
| ***G06V 10/26*** | (2022.01) |
| ***G06V 10/774*** | (2022.01) |
| ***G06V 10/82*** | (2022.01) |
| ***G16H 30/40*** | (2018.01) |

(52) U.S. Cl.
CPC .................. *G06T 7/38* (2017.01); *G06T 7/70* (2017.01); *G06V 10/26* (2022.01); *G06V 10/774* (2022.01); *G06V 10/82* (2022.01); *G16H 30/40* (2018.01); *G06T 2207/10121* (2013.01); *G06T 2207/30101* (2013.01)

(58) Field of Classification Search
CPC . G06T 2207/30101; G06T 2207/10116; G06T 2207/20081; G06T 2207/20084; G06T 7/11; A61B 6/12; A61B 6/504; A61B 6/5217; G06V 10/26; G06V 10/774; G06V 10/82; G16H 30/40
USPC .......................................................... 382/130
See application file for complete search history.

(56) References Cited

U.S. PATENT DOCUMENTS

| | | | | |
|---|---|---|---|---|
| 2012/0123238 | A1* | 5/2012 | Vaillant | G06T 7/11 600/407 |
| 2014/0187920 | A1* | 7/2014 | Millett | A61B 6/504 600/424 |
| 2014/0204124 | A1* | 7/2014 | Auvray | A61B 6/504 345/634 |
| 2014/0296703 | A1 | 10/2014 | Hong et al. | |
| 2018/0211389 | A1* | 7/2018 | Auvray | A61F 2/95 |
| 2018/0325388 | A1* | 11/2018 | Lavi | A61B 34/10 |
| 2019/0117089 | A1* | 4/2019 | Nomura | A61B 6/507 |
| 2021/0064936 | A1* | 3/2021 | Itu | G06F 18/2178 |
| 2022/0218205 | A1* | 7/2022 | Brushett | A61B 5/02007 |

OTHER PUBLICATIONS

Beier et al., "Three-Dimensional Reconstruction of Implanted Aortic Stents using Computed Tomography", Computers in Cardiology, (1995), pp. 549-552.

Reiber et al., "QCA, IVUS and OCT in Interventional cardiology in 2011", Cardiovascular Diagnosis and Therapy, (2011);1(1) pp. 57-70.

International Search report and Written Opinion of PCT/EP2021/067426, dated Oct. 11, 2021.

* cited by examiner

STENOSIS LOCALIZATION

CROSS-REFERENCE TO PRIOR APPLICATIONS

This application is the U.S. National Phase application under 35 U.S.C. § 371 of International Application No. PCT/EP2021/067426, filed on Jun. 24, 2021, which claims the benefit European Patent Application No. 20290053.6, filed on Jul. 2, 2020. These applications are hereby incorporated by reference herein.

FIELD OF THE INVENTION

The present invention relates to localizing stenoses, and relates in particular to a device for localizing a stenosis in an angiogram, to a medical system for annotating medical images of stenosis treatment and to a method for localizing a stenosis in an angiogram.

BACKGROUND OF THE INVENTION

Localizing a stenosis in an angiogram image is an important functionality that in particular enables automatic quantification and report filling-in. However, the localization task is complex, because a stenosis can be discrete and difficult to spot.

WO 2017/016885 A1 relates to quantification of a part of vascular structure. It is described to provide at least one first image comprising a spatial representation of a region of interest of a vascular structure, wherein the at least one first image comprises image data representative of a location of a part of a medical device. The medical device is configured to be used in a vascular treatment, and the part of the medical device is configured to be in a plurality of states associated with different phases of the vascular treatment. At least one second image comprising a spatial representation of the region of interest of the vascular structure is provided, wherein the at least one second image comprises image data representative of at least a part of the vascular structure in a visible and distinct manner. A location of a feature in the spatial representation of the region of interest of the vascular structure of the at least one first image is determined, wherein the feature is associated with the part of the medical device in one of the states associated with a phase of the vascular treatment. A transform relating at least one location in the at least one first image to a corresponding at least one location in the at least one second image is determined and applied to the location of the feature in the spatial representation of the region of interest of the vascular structure of the at least one first image to provide a determined location in the spatial representation of the region of interest of the vascular structure of the at least one second image. Data is output representative of the vascular structure at the determined location.

However, it has been shown that registration of the treatment sequence (fluoroscopy) to the angiographic sequence (cine) may require a rather rigid protocol, referred to as the cardiac roadmapping protocol, which may be cumbersome to follow.

SUMMARY OF THE INVENTION

There may thus be a need to provide improved and facilitated stenosis localization.

The object of the present invention is solved by the subject-matter of the independent claims; further embodiments are incorporated in the dependent claims. It should be noted that the following described aspects of the invention apply also for the device for localizing a stenosis in an angiogram, for the medical system for annotating medical images of stenosis treatment and for the method for localizing a stenosis in an angiogram.

According to the present invention, a device for localizing a stenosis in an angiogram is provided. The device comprises an image supply, a data processor and an output. The image supply is configured to provide a first image and a second image. The first image is an angiographic image that comprises image data representative of a region of interest of a vascular structure in a visible and distinct manner, wherein the vascular structure comprises at least one vessel with at least a part of a stenosis. The second image is a treatment X-ray image that comprises image data representative of at least a part of an interventional device arranged within the vascular structure in a state when the stenosis of the vascular structure is treated. The data processor is configured to identify and delineate the stenosis in the first image based on the first image and at least based on device-related content present in the second image. For the identifying and the delineating of the stenosis in the first image based on the first image and at least based on device-related content present in the second image, the data processor is configured to detect the interventional device in the second image, and to provide a direct identification of structures in the first image that are most similar to the device as detected in the second image. The output is configured to provide an identification of the stenosis for an annotation of the stenosis in at least one of the first image and second image.

This provides the effect that the indication provides support in identifying and annotating stenosis in e.g. a plurality of image data sets. The stenosis localization is thus provided in a facilitated and efficient manner.

In an example of the present invention, a device for localizing a stenosis in an angiogram is provided. The device comprises an image supply, a data processor and an output. The image supply is configured to provide a first image and a second image. The first image is an angiographic image that comprises image data representative of a region of interest of a vascular structure in a visible and distinct manner, wherein the vascular structure comprises at least one vessel with at least a part of a stenosis. The second image is a treatment image that comprises image data representative of at least a part of an interventional device arranged within the vascular structure in a state when the stenosis of the vascular structure is treated. The data processor is configured to identify and delineate the stenosis in the first image based on the first image and at least based on device-related content present in the second image. The output is configured to provide an indication of the stenosis.

In an example, for the identifying and the delineating of the stenosis in the first image based on the first image and at least based on device-related content present in the second image, the data processor is configured to detect the interventional device in the second image.

According to an example, for the detection of the interventional device in the second image, the data processor is configured to identify the device and to determine at least some of a plurality of geometric parameters relating to the device comprising at least one of the group of shape, size, orientation, bending radius, diameter and direction.

According to an example, for the identifying and the delineating of the stenosis in the first image based on the first image and at least based on device-related content present in the second image, the data processor is configured to analyze the first image and the vessel structure shown therein and to assess whether any of the geometric parameters relating to the device can be found in the first image.

According to an example, the data processor is configured to provide the identification of the stenosis in the first image based on the device-related content present in the second image in a non-registered image-based identification procedure.

In an example, the data processor is configured to provide the identification of the stenosis in the first image based on the device-related content present in the second image in a transformless procedure.

According to an example, the data processor is configured to take the first image as it is and assess the first image in view of structural parameters relating to the interventional device as detected for the interventional device without geometrical transferring or registering procedure.

According to an example, the second image comprises image data of the interventional device arranged at least partly in a treatment configuration of the stenosis. In an example, the data processor is configured to provide a self-learning algorithm to be trained with a plurality of learning pairs of first and second images.

According to an example, the data processor is configured to provide a self-learning algorithm to be trained with a plurality of input learning pairs of first and second images constituted by the first and the second images as input to the learning algorithm and by e.g. a footprint of the stenosis as characterization of the stenosis as the target output of the learning algorithm.

According to an example, the data processor comprises a convolutional network configuration.

In an option, the convolutional network configuration is provided with learning pairs of first and second images constituted by the first and the second images as input to the learning algorithm and by a footprint of the stenosis as characterization of the stenosis as the target output of the learning algorithm; and the convolutional network configuration is configured for a self-learning process to learn the relationship between the first and second images.

The term "learning pairs" refers to providing of the stenosis characteristics to make supervised learning possible.

This results in a procedure that puts a relief on the user, since the convolutional network configuration is capable of stenosis localization even with images that hardly show the stenosis based on the device mages.

According to the present invention, also a medical system for annotating medical images of stenosis treatment is provided. The system comprises an image acquisition device and a device for localizing a stenosis in an angiogram according to one of the preceding examples. The image acquisition device comprises an X-ray imaging arrangement with an X-ray source and an X-ray detector configured to provide at least one of the first and second image to the image supply unit.

According to the present invention, also a method for localizing a stenosis in an angiogram is provided. The method comprises the following steps:

- providing a first image and a second image; wherein the first image is an angiographic image that comprises image data representative of a region of interest of a vascular structure in a visible and distinct manner, wherein the vascular structure comprises at least one vessel with a stenosis; and wherein the second image is a treatment X-ray image that comprises image data representative of at least a part of an interventional device arranged within the vascular structure in a state when the stenosis of the vascular structure is treated;
- identifying and delineating the stenosis in the first image based on the first image and at least based on device-related content present in the second image; wherein, for the identifying and the delineating it is provided: detecting the interventional device in the second image, and providing a direct identification of structures in the first image that are most similar to the device as detected in the second image; and
- providing the identification of the stenosis for an annotation of the stenosis in at least one of the first image and second image.

In an example, it is provided the steps of:

- identifying and delineating the stenosis in the first image based on the first image and at least based on device-related content present in the second image; and
- providing the identification of the stenosis.

In an example, for identifying and delineating the stenosis in the first image based on the first image and at least based on device-related content present in the second image, it is provided a step of: detecting the interventional device in the second image.

In an example, the identifying of the stenosis in the first image based on the detected interventional device is provided in a transformless procedure.

According to an aspect, the procedure can also be referred to as frame-based balloon-enabled stenosis segmentation. This invention can be used by an imaging system for PCI (Percutaneous Coronary Intervention) or other endo-vascular procedures, to treat obstructed vessels.

As an advantage, there are less constraints, e.g. as compared to related to the sequence duration, injection conditions, and similarity of viewing angles. Also, no actual registration method is provided which would work fine only if no vessel distortion occurs between the treating and the angiographic phases (which is unfortunately sometimes the case, due to the intrusive and deforming action of the device). Likewise, a simple change in the placement of the injection catheter does not produce strong registration inaccuracies. This regularly otherwise happens, since the main part of the catheter may be located in the aorta where it position is much less constrained than in the thin coronary vessels. Additionally, the catheter might have changed between the angio and the fluoro sequence, for instance if the clinician has moved from a diagnostic to an interventional device. Since the present stenosis segmentation method is free of any such cardiac roadmapping protocol, such shortcomings are thus avoided.

According to an aspect, it is proposed to perform stenosis segmentation directly from a pair of treatment/angiographic images, in an end-to-end manner and without imposing a constraining protocol. Even if an AI-system is not able to directly perform proper stenosis segmentation in an angiographic image, when it is properly trained with a couple of treatment and angiographic images, it becomes capable of implicitly using the information present in the treatment phase to complement the angiographic information, ending up in the proper stenosis segmentation.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
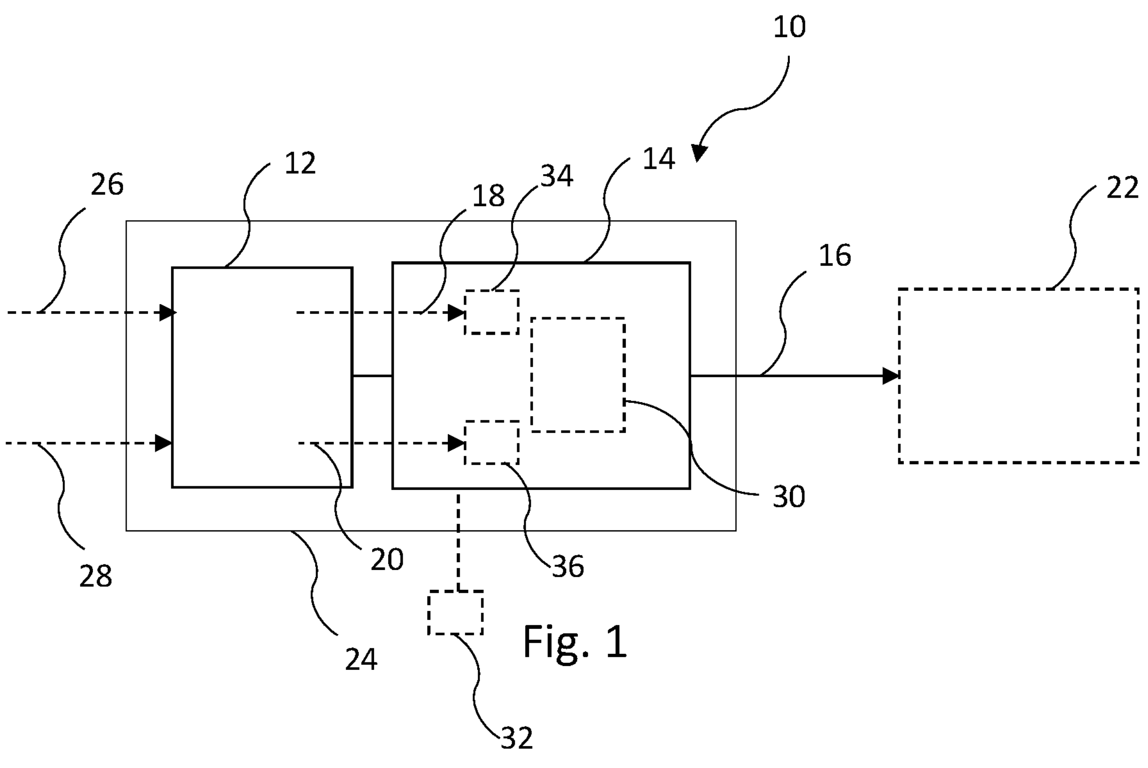
FIG. 1 schematically shows an example off a device for localizing a stenosis in an angiogram.

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

FIG. 1 schematically shows an example of a device 10 for localizing a stenosis in an angiogram. The device 10 comprises an image supply 12, a data processor 14 and an output 16. The image supply 12 is configured to provide a first image 18 and a second image 20. The first image 18 is an angiographic image that comprises image data representative of a region of interest of a vascular structure in a visible and distinct manner. The vascular structure comprises at least one vessel with at least a part of a stenosis. The second image 20 is a treatment X-ray image that comprises image data representative of at least a part of an interventional device arranged within the vascular structure in a state when the stenosis of the vascular structure is treated. The data processor 14 is configured to identify and delineate the stenosis in the first image 18 based on the first image 18 and at least based on device-related content present in the second image 20. For the identifying and the delineating of the stenosis in the first image based on the first image and at least based on device-related content present in the second image, the data processor 14 is configured to detect the interventional device in the second image, and to provide a direct identification of structures in the first image that are most similar to the device as detected in the second image. The output 16 is configured to provide an identification of the stenosis for an annotation of the stenosis in at least one of the first image and second image.

The identification can also be referred to indication of the stenosis or identifier for the stenosis. The identification of the stenosis can be provided as a visually detectable graphic element representing the location of the stenosis in the first image, like a distinct contour or color or symbol than is suitable for annotating the first image. In an example, the identification provides a marker for the location of the stenosis. For example, the identification of the stenosis represents the identified stenosis.

The image supply 12 can also be referred to as image data supply, as image input, as input or as input unit. In an example, the image supply 12 is data-connectable to an imaging arrangement source like an X-ray imaging apparatus. In an example, the image supply 12 is data-connectable to a data storage comprising at least one first image 18 and at least one second image 20. In an example, a plurality of first and second images 18, 20 are provided.

A hashed frame indicates a display 22 as an option to present the indication of the stenosis to a user.

In FIG. 1, a frame 24 indicates, as an option, that the image supply 12 and the data processor 14 are provided in a common arrangement, for example in a common housing or apparatus. In another option, the image supply 12 and the data processor 14 are provided separately.

A first hashed arrow 26 indicates the provision of the data of the first image 18 to the image supply 12. A second hashed arrow 28 indicates the provision of the data of the second image 20 to the image supply 12.

In an example, the part of a stenosis refers to a stenosis in the first image 18 that is already partly treated, but still existent.

In another example, a non-treated stenosis is present in the first image.

The data processor 14 can also be referred to as data processing arrangement, as processor unit or as processor. In an example, the data processor 14 is data-connected to the image supply 12 and the output 16.

The output 16 can also be referred to as output unit. In an example, the output 16 is data-connectable to a display arrangement.

It is noted that the term "localizing" of a stenosis refers to, for example, the designation of the location of the stenosis or also to its delineation or segmentation.

The term "angiographic image" relates to an image in which the vascular structure is shown. In an example, the angiographic image is an image of an at least partly contrast injected vasculature. The term "treatment image" relates to an image in which the interventional device is shown in a state in which it is positioned at the location of the stenosis. The treatment image contains the device that itself corresponds to the treatment.

The identification is based on a number of separate aspects from which at least some are visible in the first image 18.

The term "to identify and delineate the stenosis in the first image based on the first image and at least based on device-related content present in the second image" relates to analyzing the first image and the vessel structure shown therein and to assess whether any of the geometric parameters relating to the device can be found in the first image. In case of several instances with different matching parameters, a weighting can be provided that allows the identification of a structure that has the most promising parameters in the sense that it has the highest probability that the stenosis is identified due to the reference point of the interventional device.

The term "to identify the stenosis in the first image based on . . . " thus relates to a direct identification of structures in the first image that are most similar to the device.

Instead of any geometrical transferring or registering procedure, the first image 18 is taken as it is and assessed in view of the structural parameters relating to the interventional device, e.g. as detected for the interventional device.

In an example, a variety of different parameters is taken and each identified sub-aspect is used for assessing a part of the vascular structure shown in the first image 18 that has the highest sum of sub-aspects.

The identification is only possible for stenosis that have been processed, i.e. to be treated or about to be treated, since the second image is required showing the balloon at the stage where the treatment is about to take place or during treatment. The first image 18 shows the stenosis. If the first image 18 is taken after the treatment, the identification is no longer possible. The second image 20 requires to contain the device that corresponds to the treatment.

The identification is a registration-free procedure. It does not require further marks like wire tip or the like. The identification is purely device based, e.g. balloon-based. The process is implicitly based on the shape of the stenosis and the shape of the device when treating the stenosis.

In an example, not further shown in detail, for the identifying and the delineating of the stenosis in the first image 18 based on the first image 18 and at least based on device-related content present in the second image 20, the data processor 14 is configured to detect the interventional device in the second image 20.

The term "to detect the interventional device in the second image 20" refers to identifying the device and to determine at least some of a plurality of geometric parameters relating to the device, such as shape, size, orientation, bending radius, diameter, direction and the like.

In an example, not further shown in detail, the data processor 14 is configured to provide the identification of the stenosis in the first image 18 based on the device-related content present in the second image 20 in a non-registered image-based identification procedure.

For example, not further shown in detail, the data processor 14 is configured to provide the identification of the stenosis in the first image 18 based on the device-related content present in the second image 20 in a transformless procedure. In other words, the annotating procedure does not require a transformation of the second image to the first image, or a registration of the first and the second image. The process is relying purely on detecting geometric features in the second image and identifying matching geometric features in the first image. The connection of the first and second image is provided only as geometric pattern matching, but without any registration of the image spaces themselves.

For example, the procedure is provided in a registrationless or registrationfree manner.

The balloon image is implicitly providing a plurality of parameters. For example, a rough location is provided. Further parameters are the length, angle diameter or the like. In the position for treatment, these correspond with the stenosis. For example, the balloon is visible in the fluoro images. The steering of the catheter to bring the device in place for the treatment can be provided in many ways.

The present invention relies on the assumption that ballooning is actually done at the stenosis.

In an example, not further shown in detail, the data processor 14 is further configured to provide a segmentation of the stenosis in the first image 18 based on the device-related content present in the second image 20.

In an example, the data processor 14 is further configured to provide a segmentation of the stenosis in the first image 18 based on the detected interventional device.

In an example, not further shown in detail, the second image 20 comprises image data of the interventional device arranged at least partly in a treatment configuration of the stenosis.

In an example, the second image 20 comprises image data of the interventional device arranged at least partly within the stenosis.

In an example, not further shown in detail, the interventional device is a balloon device for treating stenosis. Further, the second image 20 comprises image data of the balloon device arranged in an at least partly inflated state.

In an option, the second image 20 is a fluoroscopic X-ray image; and the first image 18 is an X-ray image of the vascular structure with at least partly contrast injected vessels.

As an example, the data processor is configured to provide a self-learning algorithm to be trained with a plurality of learning pairs.

In an example, not further shown in detail, the data processor 14 is configured to provide a self-learning algorithm to be trained with a plurality of learning pairs of first and second images 20. In other words, the learning pairs are constituted by the first and the second images as input to the learning algorithm and by e.g. a footprint of the stenosis as characterization of the stenosis as the target output of the learning algorithm.

The characterization of the stenosis relates to image-based features, i.e. features that can actually be detected in the at least one second image. A basic aspect is the foot print, other features are shape, size, dimensions, size relations and ratios and the like.

By learning pairs, one should understand input and output data. In the present case the learning pair would be: As input: a pair of first and second images; as output: the data representative of the target stenosis. This output data can be constituted by an image containing a probability map of the stenosis and often referred to as a "heat map". The value of every pixel of this map is indicative of the probability that this pixel location corresponds to a pixel of the targeted stenosis. The heat map can therefore be seen as a valuated footprint of the stenosis (the stronger those values, the higher the probability of stenosis). But the output data can also be a symbolic representation of the stenosis (e.g. location, contours, etc.). Learning pairs are often designated by the term "Ground Truths". For instance a heat map can be created by manually delineating the stenosis footprint, and by slightly blurring this footprint to account for the probability aspect (the probability decreases as the distance to the stenosis increases). An annotated database refers to a set of learning pairs. The inputs are selected data (in the present case pairs of 1$^{st}$ and 2$^{nd}$ images), and the output are the results of manual or automatic or semi-automatic target designation (in the present case delineated stenoses.

FIG. 1 shows an as option that the data processor 14 comprises a convolutional network configuration 30.

As an option, the convolutional network configuration 30 is provided with learning pairs of first and second images constituted by the first and the second images as input to the learning algorithm and by a characterization of the stenosis as the target output of the learning algorithm; and the convolutional network configuration 30 is configured for a self-learning process to learn the relationship between the first and second images 18, 20.

The convolutional network configuration can also be referred to as neural network. For the network, a parametric system provides the function of the neural network in order to provide artificial intelligence (AI) to provide the identification of the stenosis in the first image based on the detected interventional device and based on the vessel image.

The network provides an approximator in a universal way and is trained on examples.

In an example, the network could be provided with a rough location indicator. Further, at least one of the group of a rough vision of length, diameter, shape, direction, angle, orientation and curvature could be provided. In another example, at least one of the group of a rough vision of length, diameter, shape, direction, angle, orientation and curvature are implicitly provided. As indicated above, ground-truths may be provided and heat-map, contour, mask, description parameters are applied.

In an example, the criteria can be weighted by the data processor 14.

In an example, a relationship between the two images is exploited, but never explicitly, except that these two images concur to the identification and delineation of the stenosis.

The "learning pairs" of images are also referred to as training pairs of images.

It is noted that the learning pairs relate to a pair of images as input. In an option, supervised learning is provided, e.g. when feeding the network with a pair of images as input, a correct answer is provided, i.e. the stenosis designation. It is thus further noted that when referring to learning pairs, it is not only referred to the input data, but also to the stenosis characterization.

In an example, the input of the two images is multiplied by different weights acquired by the learning process. The learning is based on taking weights and to change these and to start again. After a certain time, the weights will result in frozen weights. The self-learning usually has taken place before the normal operation of the system.

FIG. 1 shows an as option that a device segmentor 32 is provided that is configured to provide a segmentation of the interventional device. The data processor 14 is configured to provide the identification of the stenosis in the first image 18 based on the segmentation of the interventional device.

FIG. 1 shows an as another option, alternatively or in addition, that the image supply 12 is configured to provide a first plurality of the first images 18; and the data processor 14 is configured to provide a first image selection 34 that is configured to select one image of the first images 18 to provide the identification of the stenosis in the first image. Alternatively, or in addition, the image supply 12 is configured to provide a second plurality of the second images 20; and the data processor 14 is configured to provide a second image selection 36 that is configured to select one image of the second images 20 to detect the interventional device in the selected second image.

In an example, the data processor 14 comprises a first and second image selector for performing the first and second image selection.

In an example, the first and the second image selector are provided as a common image selector.

According to an example, the full extent of the stenosis is processed by several ballooning steps. At least some of those steps, in an example all of these steps, are captured by a different image, e.g. in different sequences. To reconstitute the full stenosis footprint, several outputs are agglomerated. Each of those outputs are then processed as described in the above and below examples.

In an example, not further shown in detail, the image supply 12 is configured to provide a plurality of first images 18 each comprising a part-stenosis. The processor 14 is configured to delineate or segment each part-stenosis and to merge the several stenosis parts to form a resulting stenosis. The output 16 configured to provide an indication of the resulting stenosis. Alternatively, or in addition, the image supply 12 is configured to provide a plurality of second images 20 is provided each comprising a part-treated image. The processor 14 is configured to merge the part-treated images for annotating the image data representative of at least a part of an interventional device.

In an example, a plurality of first images 18 is provided each comprising a part-stenosis, and wherein the part-stenosis are each delineated or segmented and the several stenosis parts are merged to form a resulting stenosis, which is then indicated.

In an example, provided alternatively or in addition, a plurality of second images 20 is provided each comprising a part-treated image, and wherein the part-treated images are merged for annotating the image data representative of at least a part of an interventional device.

For example, the resulting stenosis is a full stenosis.

In an example, it is provided as learning pairs to train a network as input: a vessel image, several balloon images; and as output: the description (one form or the other) of the full stenosis.

The term part-treated image refers to stenosis that are processed by multiple ballooning steps, where the balloon is being either inflated several times at the same place, but most often slightly or substantially shifted on the wire and re-inflated at those new locations.

Figure 2:
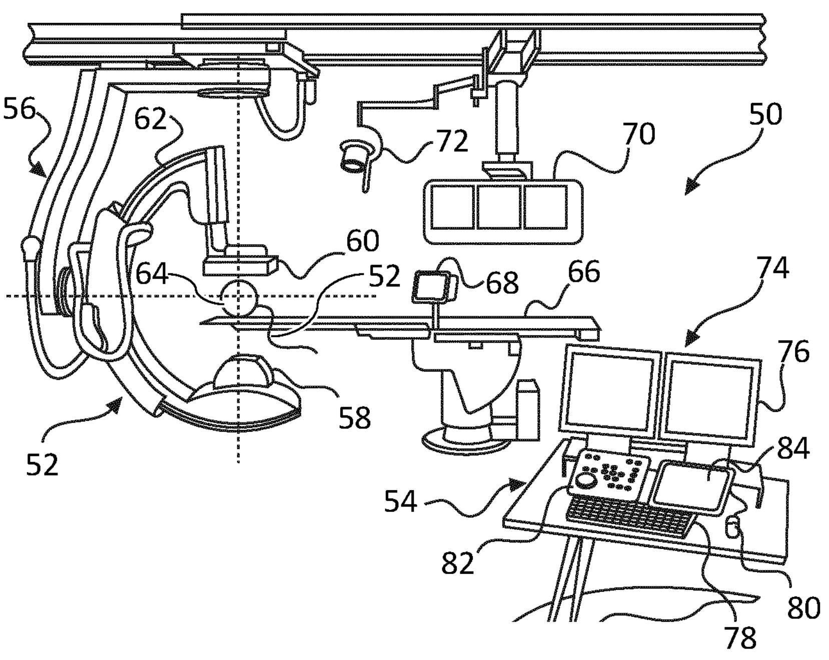
FIG. 2 shows an example of a medical system for annotating medical images of stenosis treatment.

FIG. 2 shows an example of a medical system 50 for annotating medical images of stenosis treatment. The medical system 50 comprises an image acquisition device 52 and a device 54 for localizing a stenosis in an angiogram according to one of the preceding examples. The image acquisition device 52 comprises an X-ray imaging arrangement 56 with an X-ray source 58 and an X-ray detector 60 configured to provide at least one of the first and second image to the image supply unit. The image acquisition device 52 has a C-arm 62 movably supported by a ceiling mount. The image acquisition device 52 is arranged to provide images of a subject 64 arranged on a subject support 66. A control and display interface 68 are provided next to the subject support 66. Further, a monitor arrangement 70 is indicated. Still further, lighting 72 is also provided.

The example of the device 54 for localizing a stenosis in an angiogram is provided in the context of a work station or console 74. The console 74 comprises displays 76, a keyboard 78 and a mouse 80. Further, a control console 82 and a graphical tablet 84 are indicated.

In an example, the self-learning has taken place when the system is operated.

Figure 3:
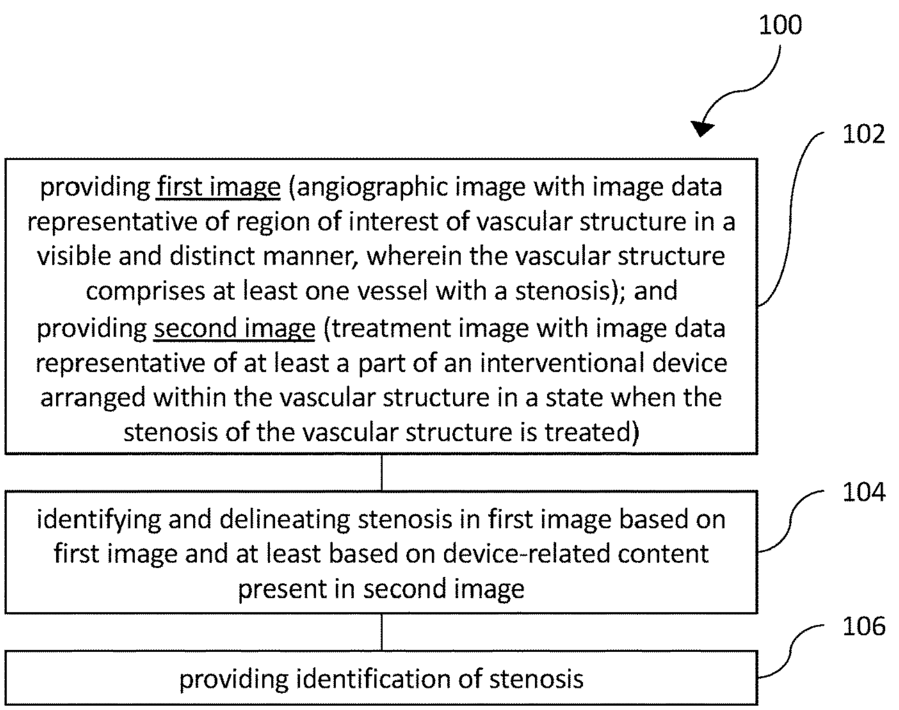
FIG. 3 shows basic steps of an example of a method for localizing a stenosis in an angiogram.

FIG. 3 shows basic steps of an example of a method 100 for localizing a stenosis in an angiogram. The method 100 comprises the following steps: In a first step 102, also referred to as step a), a first image and a second image are provided. The first image is an angiographic image that comprises image data representative of a region of interest of a vascular structure in a visible and distinct manner, wherein the vascular structure comprises at least one vessel with a stenosis. The second image is a treatment X-ray image that comprises image data representative of at least a part of an interventional device arranged within the vascular structure in a state when the stenosis of the vascular structure is treated. In a second step 104, also referred to as step b), the stenosis is identified and delineated in the first image based on the first image and at least based on device-related content present in the second image. For the identifying and the delineating it is provided detecting the interventional device in the second image, and providing a direct identification of structures in the first image that are most similar to the device as detected in the second image. In a third step 106, also referred to as step c), the identification of the stenosis is provided for an annotation of the stenosis in at least one of the first image and second image.

In an example, the identifying of the stenosis in the first image based on the detected interventional device is provided in a transformless procedure.

Figure 4:
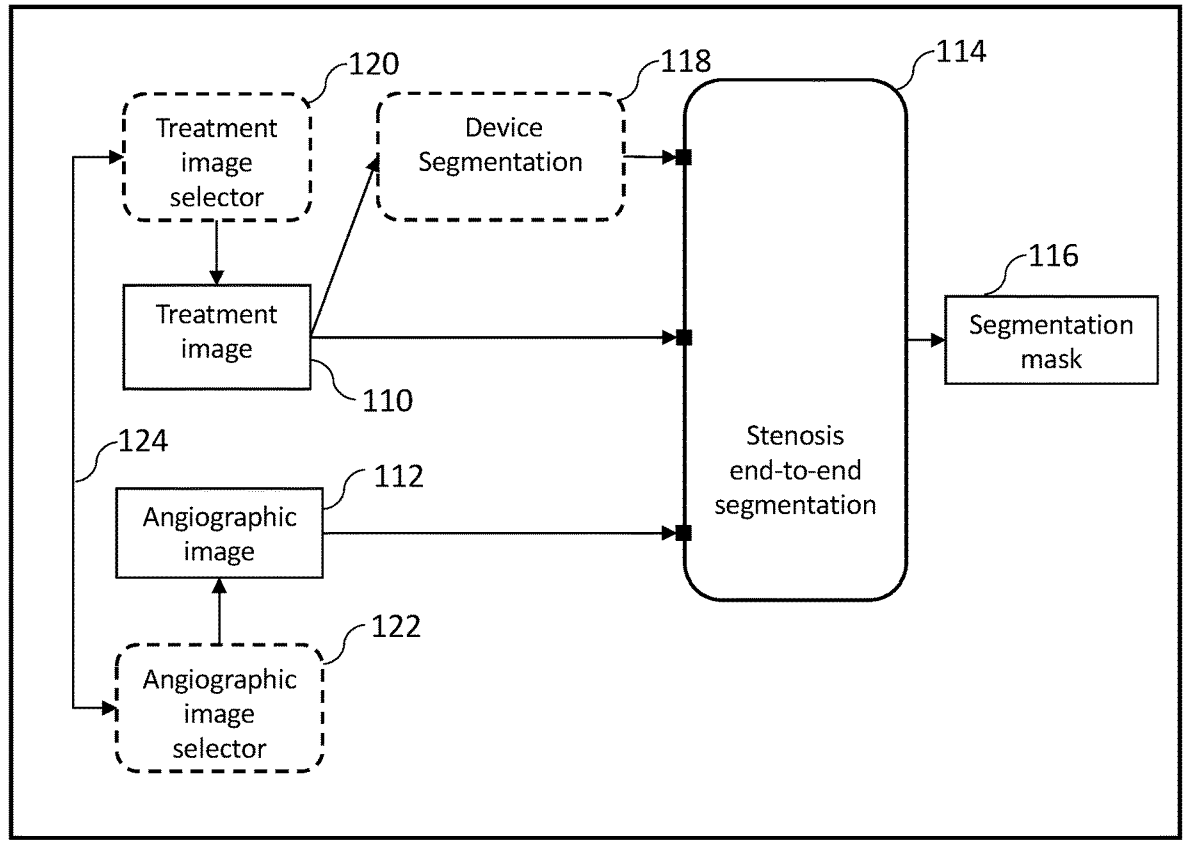
FIG. 4 shows another example of a workflow of a method.

FIG. 4 shows another example of a workflow of a method. FIG. 4 is showing a diagram illustrating basic steps of another example of a method. In a first step, a treatment image 110 and an angiographic image 112 are provided. Both are provided to a stenosis end-to-end segmentation 114 which results in a segmentation mask 116. In an option, the treatment image is provided to a device segmentation 118 and the result is provided to the stenosis end-to-end segmentation 114. In a further option, a treatment image selection 120 is provided as a sub-step in order to provide the treatment image 110. In a further option, provided in addition or alternatively, an angiographic image selection 122 is provided as a sub-step in order to provide the angiographic image 112. The treatment image selection 120 and the angiographic image selection 122 can be provided in a linked manner.

The treatment image 110 may be provided as an input of an image acquired during stenosis treatment (e.g. under fluoroscopy), where the stenosis is not made visible by contrast agent. This treatment image must contain the interventional device when it is present within the stenosis.

The angiographic image 112 may be provided as an angiographic image that contains the stenosis being treated or that will be treated or that has already been treated. As any angiographic image, a contrast agent has been injected, which has made the stenosis visible (though maybe in a flimsy way).

The treatment image selection 120 (also referred to as treatment image selector) option may be provided to be responsible for the selection of the treatment image. Because the stenosis is not visible in the treatment sequences, this can only be insured by some property of the device (for instance a balloon being inflated). The selection can therefore be achieved by the proper detection of this property. For instance, it can consist in detecting a balloon expansion. This may or may not involve learning techniques. But the treatment image might also be simply designated through human interaction.

The angiographic image selection 122 (also referred to as angiographic image selector) option may be provided to be responsible for the selection of the angiographic image. This image must correspond to the already selected treatment image (hence a diagram link 124 between the two image selection blocks). Simple viewing angle and contrast information might be involved in this selection process. For instance, the target image might be designated as follows: an angiographic image that is correctly injected and that pertains to a sequence acquired roughly under the same angulation as the one used for the treatment image. Temporal proximity between the treatment and the angiographic images might also be involved. But the angiographic image might also be simply designated through human interaction.

In the diagram, the link 124 between the two image selections is bi-directional. This refers to the fact that the angiogram image might be the problem target: segmenting the treated stenosis in this image. In this case, the treatment image selection is subjected to that choice and must find a treatment image in which a device is in a state indicating its presence within the stenosis. Again, viewing angles and temporal proximity might be resorted to in order to designate (for instance) a proper balloon expansion image.

The device segmentation option is provided such that the device can be segmented and the resulting device footprint used in the subsequent step. Traditional Computer-Vision or AI-based methods can be involved in that step. Actually, such a block can also be part or feed the treatment image selection block.

In an option, a device segmentation step is provided. However, an end-to-end segmentation is achieved through the presentation of a treatment and angiographic image pair. The treatment image must contain the device at a moment where it is implicitly localized in the stenosis. For instance, this is always the case with an inflated balloon. The angiographic image contains the stenosis being treated or that will be treated or that has been treated.

The stenosis end-to-end segmentation is a core aspect. In its purest version, it receives two entries which are simply a compliant pair of treatment/angiographic images. Typically, this block is a two entry image convolution network trained to produce the stenosis footprint as seen in the angiographic image. The treatment image is used as a guide to the right solution. It is rather striking that, when annotating the necessary material (the stenosis footprint), a human annotator also tends to spot and identify the stenosis thanks to the observation of the device image. In an optional variation, the network can also be fed with a third image constituted by the device footprint.

Figure 5:
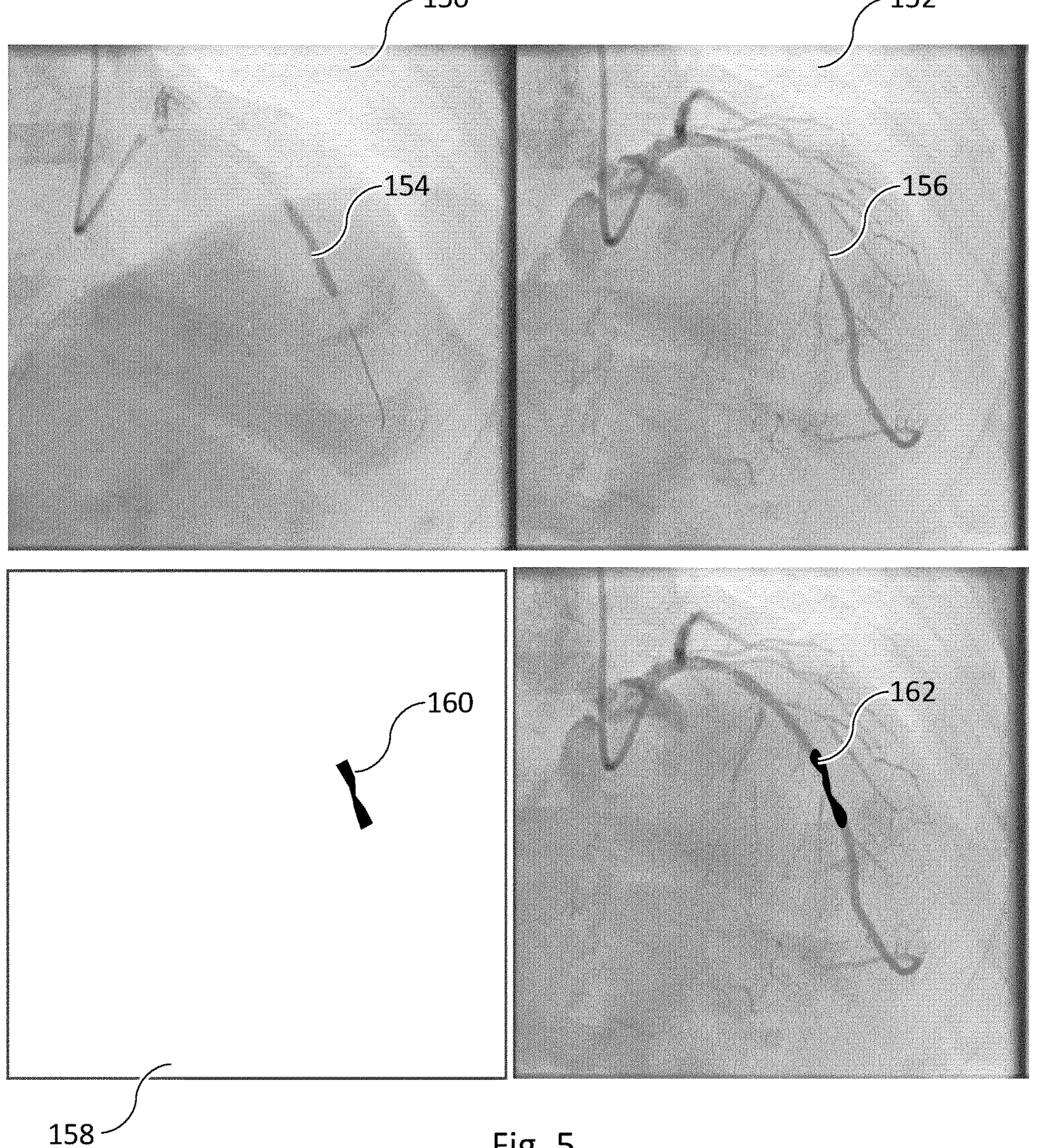
FIG. 5 illustrates image data of different steps of an example of a method.

FIG. 5 illustrates image data of different steps of an example of a method. The top-left image corresponds to an X-ray ballooning image 150, e.g. the treatment image indicating a balloon 154. Top-right is the contrast-filled angiographic image 152 (thus also an X-ray image) featuring the vessel of interest and, on this vessel, a target stenosis 156. For the sake of illustration, a rather visible stenosis (clear diameter reduction) is chosen. The first row of images corresponds to the entry (and image pair, i.e. the first images and second images), as it would be provided to the network for learning the output that is represented by the bottom-left image 158, showing the ideal delineation 160 of the stenosis (ground-truth). The lower left image thus only shows the delineation 160 of the stenosis. The bottom-right image is the output of the network in a generalization phase annotating a stenosis 162 in an X-ray image.

It is noted that the term "subject" may also be referred to as individual. The "subject" may further also be referred to as patient, although it is noted that this term does not indicate whether any illness or disease is actually present with the subject.

In an example, a computer program is provided enabling a processor to carry out a method of one of the preceding examples.

In an example, a computer program or program element for controlling an apparatus according to one of the examples above is provided, which program or program element, when being executed by a processing unit, is adapted to perform the method steps of one of the method examples above.

In an example, a computer readable medium having stored the program element of the preceding example is provided.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit or be distributed over more than one computer units, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

Aspects of the invention may be implemented in a computer program product, which may be a collection of computer program instructions stored on a computer readable storage device which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

As discussed above, the processing unit, for instance a controller implements the control method. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

This exemplary embodiment of the invention covers both, a computer program that right from the beginning uses the invention and a computer program that by means of an up-date turns an existing program into a program that uses the invention. Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for localizing a stenosis in an angiogram, the device comprising:

an image supply configured to provide a first plurality of angiographic images and a second plurality of treatment images;

wherein each of the first plurality of angiographic images comprises image data representative of a region of interest of a vascular structure, wherein the vascular structure comprises at least one vessel with at least a part of a stenosis, and;

wherein each of the second plurality of treatment images comprises image data representative of at least a part of an interventional device arranged within the vascular structure in a state when the stenosis of the vascular structure is treated; and a data processor configured to:

select a second image from the second plurality of treatment images based on a detection of a property of the interventional device;

for at least one first image from the first plurality of angiographic images, identify a part-stenosis in the first image based on a direct identification of structures in the first image that are most similar to the interventional device as detected in the second image;

delineate the part-stenosis from the at least one first image; and provide an identification of a full stenosis by merging together the part-stenosis for an annotation of the stenosis in at least one of the first image and second image.

2. The device according to claim 1, wherein, the data processor configured to identify a part-stenosis in the first image based on a direct identification of structures in the first image that are most similar to the interventional device as detected in the second image is further configured to identify the interventional device in the second image and to determine at least some of a plurality of geometric parameters relating to the interventional device comprising at least one of the group of shape, size, orientation, bending radius, diameter and direction.

3. The device according to claim 2, wherein, the data processor configured to identify a part-stenosis in the first image based on a direct identification of structures in the first image that are most similar to the interventional device as detected in the second image is further configured to analyze whether any of the plurality of geometric parameters relating to the interventional device can be found in vessel structures from the first image.

4. The device according to claim 1, wherein the data processor configured to identify the part-stenosis in the first image is configured to provide the identification of the part-stenosis in the first image based on the device-related content present in the second image in a non-registered image based identification procedure.

5. The device according to claim 1, wherein the data processor is configured to take the first image as it is and assess the first image in view of structural parameters relating to the interventional device as detected for the interventional device without geometrical transferring or registering procedure.

6. The device according to claim 1, wherein the data processor is further configured to provide a segmentation of the part-stenosis in the first image based on device-related content present in the second image.

7. The device according to claim 1, wherein the second image comprises image data of the interventional device arranged at least partly in a treatment configuration of the stenosis.

8. The device according to claim 1, wherein the interventional device is a balloon device for treating stenosis; and wherein the second image comprises image data of the balloon device arranged in an at least partly inflated state.

9. The device according to claim 1, wherein the data processor is configured to provide a self-learning algorithm to be trained with a plurality of learning pairs constituted by the first and the second images as input to the learning algorithm and by a footprint of the stenosis as characterization of the stenosis as the target output of the learning algorithm.

10. The device according to claim 1, wherein the data processor comprises a convolutional network configuration; and wherein the convolutional network configuration is provided with learning pairs of first and second images constituted by the first and the second images as input to the learning algorithm and by a footprint of the stenosis as characterization of the stenosis as target output of the learning algorithm; and the convolutional network configuration is configured for a self-learning process to learn the relationship between the first and second images.

11. The device according to claim 1, wherein a device segmentor is provided that is configured to provide a segmentation of the interventional device; and wherein the data processor is configured to provide the identification of the stenosis in the first image based on the segmentation of the interventional device.

12. The device according to claim 1, wherein:

the image supply is configured to provide: a plurality of first images each comprising a part-stenosis; the data processor is configured to delineate or segment each part-stenosis and to merge the several stenosis parts to form a resulting stenosis; and the data processor is configured to provide an indication of the resulting stenosis; and/or the image supply is configured to provide a plurality of second images each comprising a part-treated image; and the data processor is configured to merge the part-treated images for annotating the image data representative of at least a part of an interventional device.

13. A medical system for annotating medical images of stenosis treatment, the system comprising:

a device for localizing a stenosis in an angiogram according to claim 1; and an image acquisition device comprising an X-ray imaging arrangement with an Xray source and an X-ray detector configured to provide at least one of the first and second image to the image supply unit.

14. A method for localizing a stenosis in an angiogram, the method comprising:

providing a first plurality of angiographic images and a second plurality of treatment images, wherein each of the first plurality of angiographic images comprises image data representative of a region of interest of a vascular structure, wherein the vascular structure comprises at least one vessel with at least a part of a stenosis, and wherein each of the second plurality of treatment images comprises image data representative of at least a part of an interventional device arranged within the vascular structure in a state when the stenosis of the vascular structure is treated;

selecting a second image from the second plurality of treatment images based on a detection of a property of the interventional device for at least one first image from the first plurality of angiographic images, identifying a part-stenosis in the first image based on a direct identification of structures in the first image that are most similar to the interventional device as detected in the second image;

delineating the part-stenosis from the at least one first image; and providing an identification of a full stenosis by merging together the part-stenosis for an annotation of the stenosis in at least one of the first image and second image.

15. A non-transitory computer-readable storage medium having stored a computer program comprising instructions, which, when executed by a processor, cause the processor to:

receive a first plurality of angiographic images and a second plurality of treatment images, wherein each of the first plurality of angiographic images comprises image data representative of a region of interest of a vascular structure, wherein the vascular structure comprises at least one vessel with at least a part of a stenosis, and wherein each of the second plurality of treatment images comprises image data representative of at least a part of an interventional device arranged within the vascular structure in a state when the stenosis of the vascular structure is treated;

select a second image from the second plurality of treatment images based on a detection of a property of the interventional device for at least one first image from the first plurality of angiographic images, identify a part-stenosis in the first image based on a direct identification of structures in the first image that are most similar to the interventional device as detected in the second image;

delineate the part-stenosis from the at least one first image; and provide an identification of a full stenosis by merging together the part-stenosis for an annotation of the stenosis in at least one of the first image and second image.

* * * * *